(12) United States Patent
Guo et al.

(10) Patent No.: US 9,669,186 B2
(45) Date of Patent: Jun. 6, 2017

(54) METHOD OF MANUFACTURING A PEELABLE ATRAUMATIC TIP AND BODY FOR A CATHETER OR SHEATH

(71) Applicant: St. Jude Medical Atrial Fibrillation Division, Maple Grove, MN (US)

(72) Inventors: Xiaoping Guo, Eden Prairie, MN (US); Richard E. Stehr, Stillwater, MN (US); Vitaliy G. Epshteyn, Maple Grove, MN (US); Bruce P. Holman, Champlin, MN (US); Donald A. Sauter, Victoria, MN (US); Chad A. Thorstenson, Andover, MN (US); Daniel J. Potter, Stillwater, MN (US); Nalin S. Perera, Santa Clarita, CA (US)

(73) Assignee: ST. JUDE MEDICAL ATRIAL FIBRILLATION DIVISION, Maple Grove, MN (US)

( * ) Notice: Subject to any disclaimer, the term of this patent is extended or adjusted under 35 U.S.C. 154(b) by 358 days.

(21) Appl. No.: 14/179,391

(22) Filed: Feb. 12, 2014

(65) Prior Publication Data

US 2014/0157573 A1 Jun. 12, 2014

Related U.S. Application Data

(62) Division of application No. 11/911,190, filed as application No. PCT/US2006/016372 on Apr. 28, 2005, now Pat. No. 8,657,789.

(60) Provisional application No. 60/675,973, filed on Apr. 28, 2005, provisional application No. 60/677,423, filed on May 3, 2005.

(51) Int. Cl.
*A61M 25/00* (2006.01)
*A61M 25/06* (2006.01)

(52) U.S. Cl.
CPC ...... *A61M 25/001* (2013.01); *A61M 25/0668* (2013.01); *A61M 2025/0687* (2013.01); *Y10T 29/49826* (2015.01)

(58) Field of Classification Search
CPC ....... B29C 66/5221; A61M 2025/0687; A61M 25/001; A61M 25/0668
See application file for complete search history.

(56) References Cited

U.S. PATENT DOCUMENTS

2004/0267203 A1* 12/2004 Potter ............... A61M 25/0108
604/164.05

* cited by examiner

Primary Examiner — Christopher Schatz

(57) ABSTRACT

A method of manufacturing a splittable/peelable tubular body of a catheter or sheath wherein the tubular body has a splittable/peelable atraumatic tip is disclosed. The atraumatic tip is generally softer than the tubular body. The tubular body and atraumatic tip each comprise a peel mechanism longitudinally extending along their respective lengths. The peel mechanisms are formed by longitudinally extending regions of interfacial bonding between first and second longitudinally extending strips of polymer material. Each strip forms at least a portion of an outer circumferential surface of the tubular body and atraumatic tip. A region of stress concentration extends along the region of interfacial bonding. The stress concentration facilitates the splitting of the tubular body and atraumatic tip along their respective peel mechanisms.

18 Claims, 10 Drawing Sheets

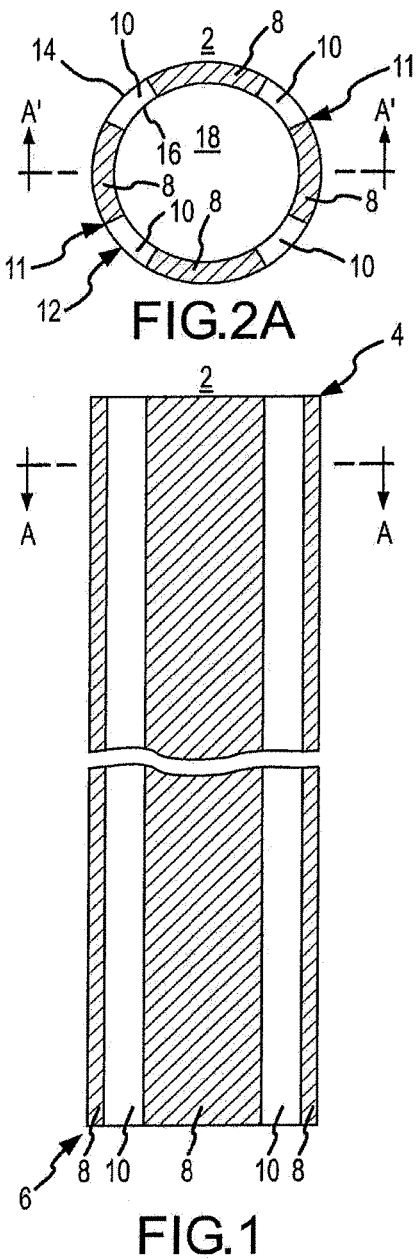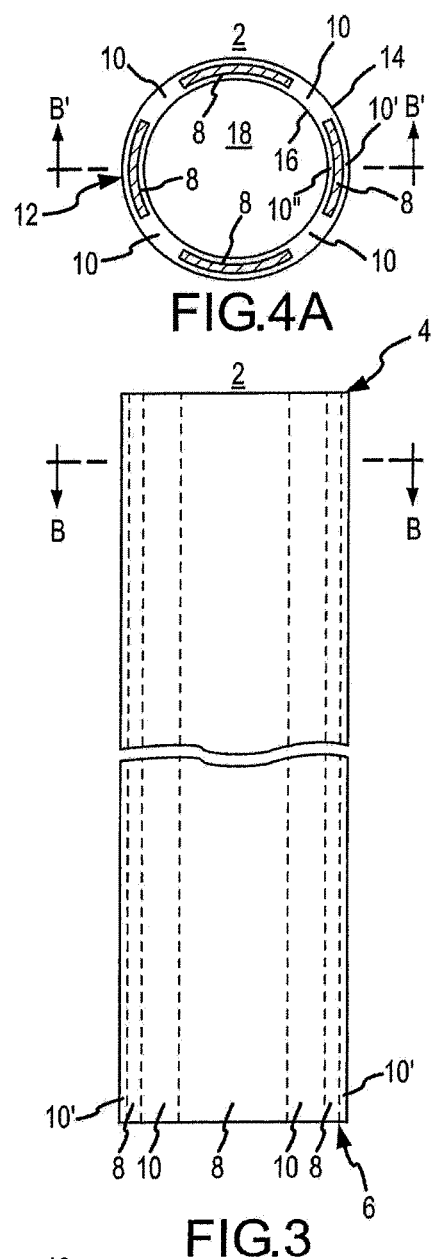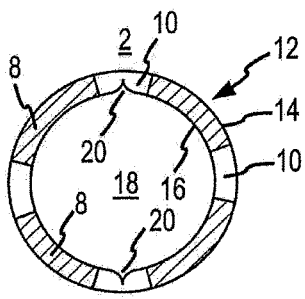

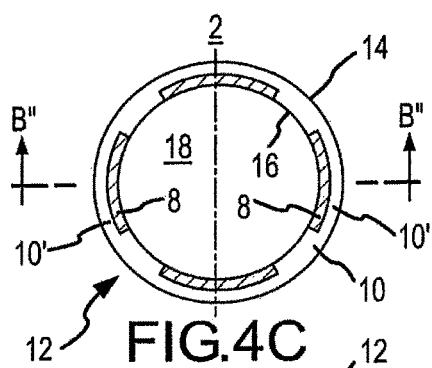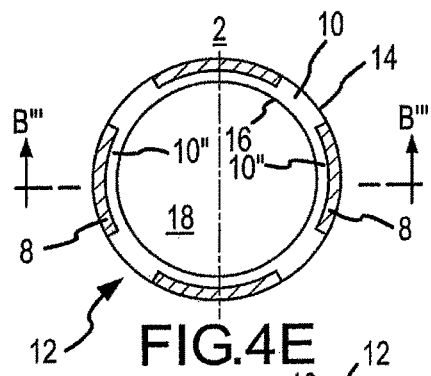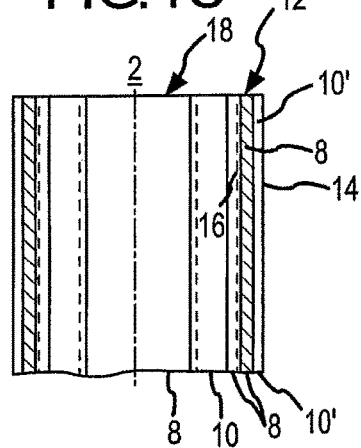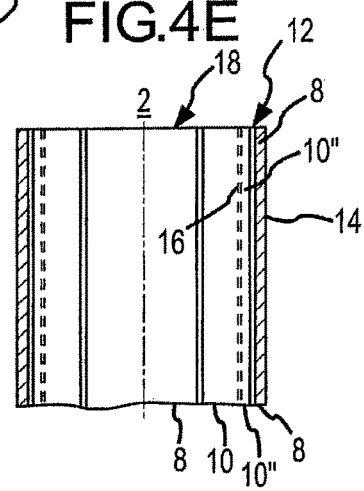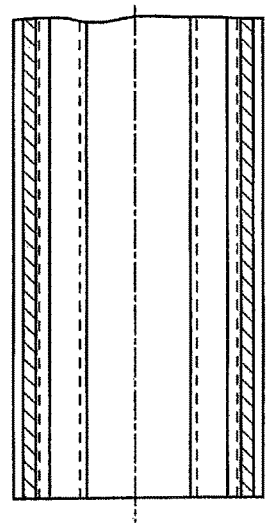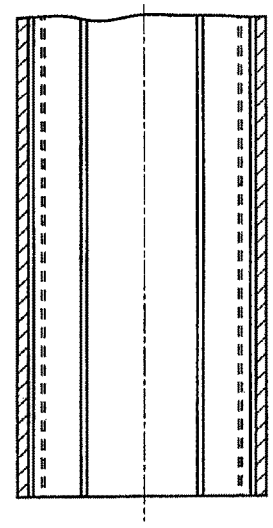
FIG.4D  FIG.4F

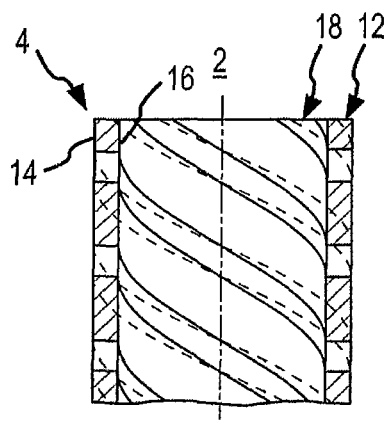 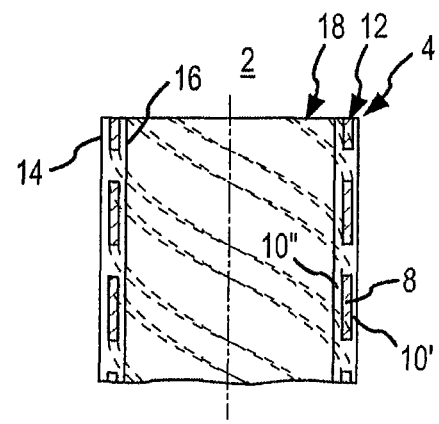
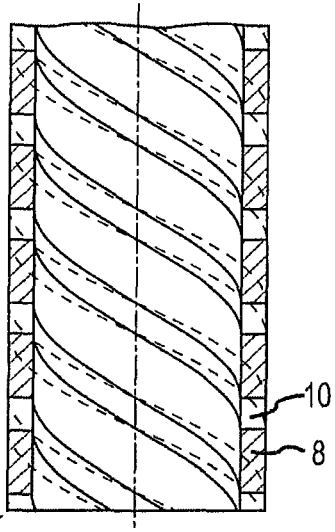 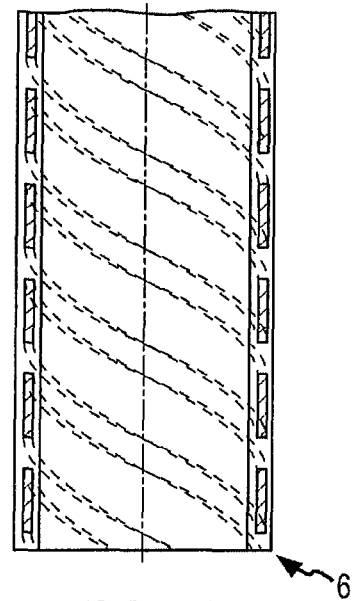
FIG.6B                    FIG.8B

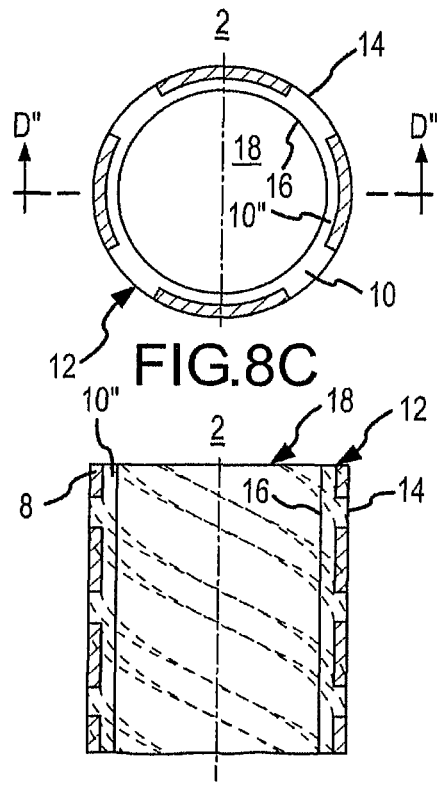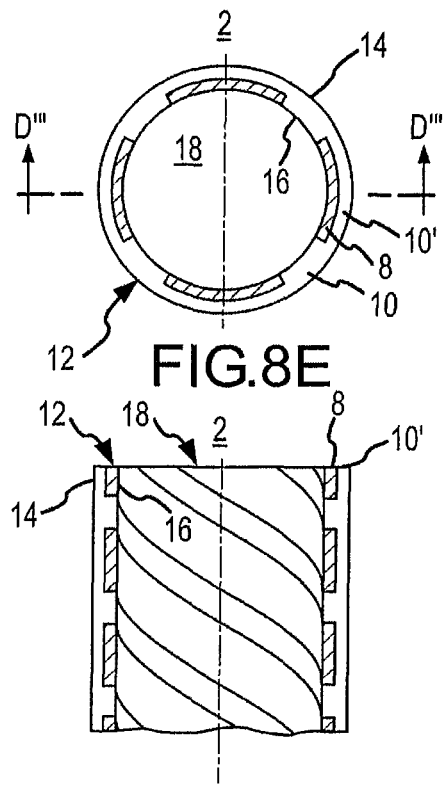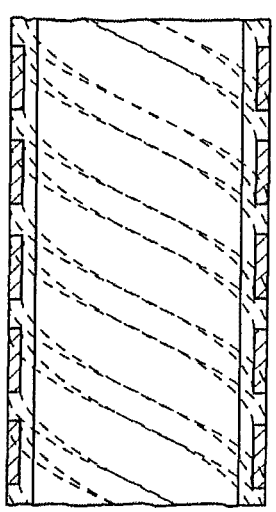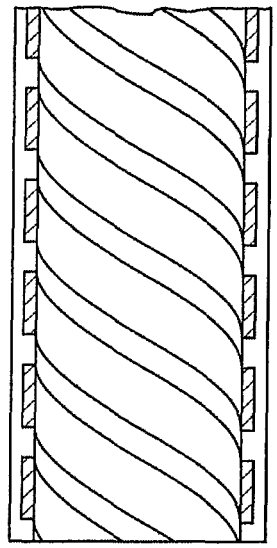
FIG.8D  FIG.8F

METHOD OF MANUFACTURING A PEELABLE ATRAUMATIC TIP AND BODY FOR A CATHETER OR SHEATH

CROSS-REFERENCE TO RELATED APPLICATIONS

This application is a division of U.S. patent application Ser. No. 11/911,190, filed Oct. 10, 2007, which is a National Stage Entry of International Application No. PCT/US06/16372, filed Apr. 28, 2006, and claims the benefit of U.S. Provisional Application Ser. No. 60/675,973, filed Apr. 28, 2005, and U.S. Provisional Application Ser. No. 60/677,423, filed May 3, 2005.

BACKGROUND OF THE INVENTION

The present invention relates to bodies for catheters and sheaths, and to tips for use in conjunction with such catheters and sheaths, as wells as to methods of manufacturing and using the same. More particularly, the present invention relates to splittable and radiopaque bodies and tips, and to methods of manufacturing and using such bodies and tips.

Catheters and sheaths are commonly manufactured with splittable (i.e., peelable or peel-away) type tubular bodies that allow the catheter or sheath to be removed from about an implanted medical device (e.g., pacemaker leads) without disturbing the device. Prior art tubular bodies are formed with peeling grooves that extend longitudinally along the inner or outer circumferential surfaces of their walls in order to make the tubular bodies splittable. Providing such peeling grooves is a difficult and expensive manufacturing process.

Other catheters and sheaths are commonly manufactured with tubular bodies having radiopaque distal tips. Such catheters and sheaths are used in cardiovascular procedures and other medical procedures. The radiopaque distal tip may be viewed within a patient's body via an X-ray fluoroscope or other imaging system, thereby allowing a physician to position the tubular body as required during a procedure.

Prior art tubular bodies with radiopaque distal tips often use precious heavy metals (e.g., gold, platinum, tantalum) to achieve sufficient tip radiopacity. For example, a thin band of a precious heavy metal is imbedded in the distal tip of each such prior art tubular body. As a result, such prior art tubular bodies end up being quite expensive because of the high cost of the precious heavy metals and the labor intensive manufacturing processes used to manufacture such tubular bodies.

Tubular bodies are made from polymeric materials that may not be chemically compatible with the precious metal used to form the radiopaque distal band. As such, the distal band may not adhere to the material matrix of the tubular body, causing potential material separation and a discontinuity in mechanical strength.

Where a tubular body with a radiopaque distal tip also needs to be splittable to allow its removal from a patient without disturbing an implanted medical device, the thin band of precious heavy metal must be provided with a peeling groove that coincides with the peeling groove in the tubular body's wall. This adds further difficulty and expense to an already difficult and expensive manufacturing process.

There is a need in the art for a splittable and/or radiopaque tubular body that utilizes less costly materials, is less labor intensive to manufacture, and is less likely to fail during a medical procedure due to material separation. There is also a need for methods of manufacturing and using such a tubular body.

BRIEF SUMMARY OF THE INVENTION

The present invention, in one embodiment, is a peelable atraumatic tip for a peelable body of a catheter or sheath. The tip comprises a peel mechanism longitudinally extending along the tip. The tip may be generally softer than the body.

In one embodiment, the peel mechanism is formed by a longitudinally extending region of interfacial bonding between first and second longitudinally extending strips of material. The material of the first strip may have a greater amount of radiopaque filler than the polymer material of the second strip. Each strip may form at least a portion of an outer circumferential surface of the tubular body. A region of stress concentration extends along the region of interfacial bonding. The stress concentration facilitates the splitting of the tip along the peel mechanism.

In another embodiment, the materials of the first and second strips differ in that the material of the first strip is loaded with a greater amount of inorganic filler than the material of the second strip. The material of the first strip may comprise a greater amount of radiopaque filler than the material of the second strip.

In yet another embodiment, a polymeric material of the first strip is not chemically compatible with a polymeric material of the second strip. Consequently, a polymer compatibilizer is introduced into at least one of the polymer materials to improve melt adhesion between the first and second strips of polymer material.

In one embodiment, the peel mechanism is formed by a peel groove. The peel mechanism may be formed, for example, by a score/skive line. The tip may further comprise a circular radiopaque band imbedded below an outer circumferential surface of the tip. The band includes a notch aligned with the peel mechanism.

In another embodiment, the tip also includes third and fourth longitudinally extending strips of material. In this embodiment the third strip has a greater amount of radiopaque filler than the fourth strip and the third strip is wider than the first strip.

The present invention, in yet another embodiment, is a method of attaching a peelable atraumatic tip to a distal end of a peelable tubular body of a catheter or sheath. The method comprises placing the tubular body on a mandrel, and placing the tip onto the distal end of the body. The body includes a first peel mechanism longitudinally extending along the body, and the tip includes a second peel mechanism longitudinally extending along the tip. The second peel mechanism is aligned to longitudinally coincide with the first peel mechanism. The tip is joined to the distal end of the body.

In one embodiment, the second peel mechanism is formed by a longitudinally extending region of interfacial bonding between first and second longitudinally extending strips of material. The second peel mechanism may be formed by a peel groove. Alternatively, the second peel mechanism may be formed by a score/skive line.

The present invention, in one embodiment, is a catheter or sheath comprising a splittable tubular body and a splittable atraumatic tip. The splittable tubular body includes a first peel mechanism longitudinally extending along the body. The splittable atraumatic tip includes a second peel mechanism aligned with the first peel mechanism and longitudinally extending along the tip. The second peel mechanism is formed by a longitudinally extending region of interfacial bonding between first and second longitudinally extending strips of material.

The present invention, in one embodiment, is a catheter or sheath comprising a splittable tubular body and a splittable atraumatic tip. The splittable tubular body includes a first peel mechanism longitudinally extending along the body. The first peel mechanism is formed by a longitudinally-extending region of interfacial bonding between first and second longitudinally extending strips of material. The splittable atraumatic tip includes a second peel mechanism aligned with the first peel mechanism and longitudinally extending along the tip.

The present invention, in one embodiment, is a splittable device for coupling to a proximal end of a splittable tubular body for a catheter or sheath. The device comprises a housing including a split line formed by a longitudinally extending region of interfacial bonding between first and second longitudinally extending strips of polymer material. In various embodiments, the device is, for example, an interlock, a valve, a junction, or a fitting.

The present invention, in yet another embodiment, is a method of attaching an atraumatic tip to a distal end of a tubular body of a catheter or sheath. The method is as follows. The tubular body is provided and caused to have a first pre-curved portion existing in a first plane. The tip is provided and includes a first radiopaque strip longitudinally extending along the tip and existing in a second plane. The tip is placed onto the distal end of the body such that the first and second planes align, and the tip is joined to the distal end.

The present invention, in another embodiment, is a catheter or sheath including a tubular body and an atraumatic tip coupled to the distal end of the body. The tubular body includes a first pre-curved portion existing in a first plane. The atraumatic tip includes a first radiopaque strip longitudinally extending along the tip and existing in the first plane.

BRIEF DESCRIPTION OF THE DRAWINGS

FIG. 1 is a side elevation view of the present invention according to a first embodiment, including le/peelable tubular body for a catheter or sheath, wherein the tubular body includes a distal end and a proximal end and is formed of at least two integral longitudinal strips of different material.

FIG. 2A is a latitudinal cross-sectional view of the first embodiment of the tubular body taken through section line A-A in FIG. 1.

FIG. 3 is a side elevation view of the present invention according to a second embodiment, including a splittable tubular body for a catheter or sheath, wherein the tubular body includes a distal end and a proximal end and is formed of at least two integral longitudinal strips of different material.

FIG. 4A is a latitudinal cross-sectional view of the second embodiment of the tubular body taken through section line B-B in FIG. 3.

FIG. 4C is a latitudinal cross-sectional view of a first variation of the second embodiment of the tubular body taken through section line B-B in FIG. 3.

FIG. 4D is a longitudinal cross-sectional view of the first variation of the second embodiment of the tubular body taken through section line B"-B" in FIG. 4C.

FIG. 4E is a latitudinal cross-sectional view of a second variation of the second embodiment of the tubular body taken through section line B-B in FIG. 3.

FIG. 4F is a longitudinal cross-sectional view of the second variation of the second embodiment of the tubular body taken through section line B'"-B'" in FIG. 4E.

FIG. 6B is a longitudinal cross-sectional view of the third embodiment of the tubular body taken through section line C'-C' in FIG. 6A.

FIG. 8B is a longitudinal cross-sectional view of the fourth embodiment of the tubular body taken through section line D'-D' in FIG. 8A.

FIG. 8C is a latitudinal cross-sectional view of a first variation of the fourth embodiment of the tubular body taken through section line D-D in FIG. 7.

FIG. 8D is a longitudinal cross-sectional view of the first variation of the fourth embodiment of the tubular body taken through section line D"-D" in FIG. 8C.

FIG. 8E is a latitudinal cross-sectional view of a second variation of the fourth embodiment of the tubular body taken through section line D-D in FIG. 7.

FIG. 8F is a longitudinal cross-sectional view of the second variation of the fourth embodiment of the tubular body taken through section line D'"-D'" in FIG. 8E.

FIG. 9 is similar to FIG. 2A, but is a cross-sectional view of the present invention according to a fifth embodiment, including a splittable tubular body, wherein the tubular body has integral peel grooves that can be located in either the first or the second longitudinal strips.

DETAILED DESCRIPTION OF THE INVENTION

Figure 2B:
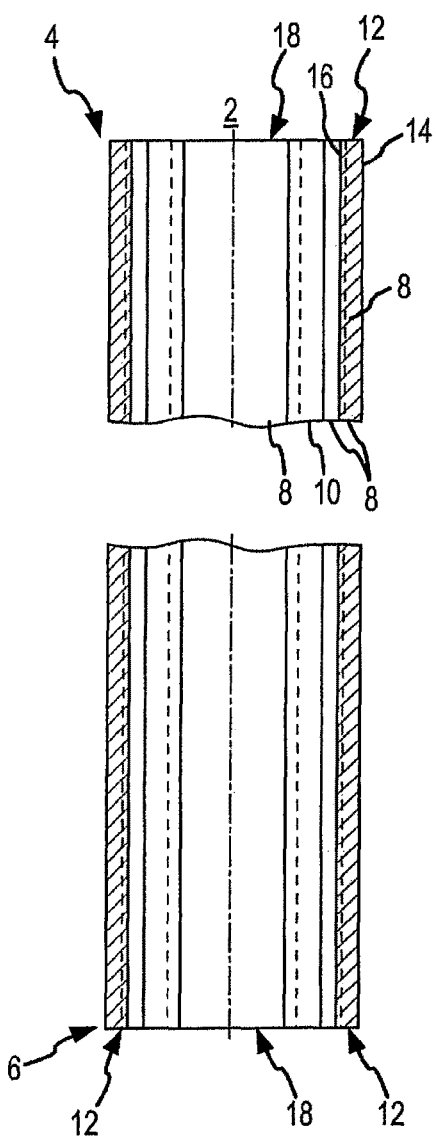
FIG. 2B is a longitudinal cross-sectional view of the first embodiment of the tubular body taken through section line A'-A' in FIG. 2A.

FIG. 1 is a side elevational view of the present invention according to a first embodiment, including a splittable (i.e., peel-away type) tubular body 2 for a catheter or sheath. The tubular body 2 includes a distal end 4 and a proximal end 6. In the embodiment shown in FIG. 1, the tubular body 2 is formed of at least two integral longitudinal strips 8, 10 of different materials, (e.g., a first polymer and a second polymer). As indicated in FIG. 1, each strip 8, 10 may extend the full length of the tubular body 2 in a generally straight manner.

The strips 8, 10 will be referred to herein as the first strip 8 and the second strip 10. The material of the first strip 8 will be sufficiently different from the material of the second strip 10 so as to form a stress concentration along the interfacial zones (i.e., borders) 11 between the two strips 8, 10. The stress concentration forms a peel line 11 that acts like a built-in peel groove. As a result, the tubular body 2 may be readily splittable although it lacks an actual peel groove.

The dissimilarity between the materials used to form the strips 8, 10 need only be sufficient enough to create a stress concentration that acts as a built-in peel groove. This may be accomplished in different ways, including the following ways.

The materials used for the strips 8, 10 may be from a first polymer, and the second strip 10 may be constructed from a second polymer, generally the same, but can also differ. The polymer used for the first strip 8 may have a different molecular orientation than the polymer used for the second strip 10. In one embodiment, the polymer material used for the first strip 8 is a polymer with flow-induced axial molecular orientation, and the polymer used for the second strip 10 is a polymer having little or no flow-induced axial molecular orientation. In such an embodiment, the tear strength along the flow-induced orientation direction for the polymeric material used for the first strip 8 will decrease due to the mechanical anisotropy induced by the molecular chain alignment. Conversely, due to its low level of mechanical anisotropy, the polymeric material used for the second strip 10 will have any one or all of the following attributes: high tear strength; high mechanical strength, high torquability; and high kink resistance. Examples of materials that can be used for the first strip 8 and are easily molecularly oriented along the flow direction during polymer processing include, among other materials, crystal polymers like Ticona Vectra™, LKX 1107, and LKX 1113.

The base polymer materials used for the first and second strips 8, 10 can be chemically the same or similar, except, the material used for the first strip 8 is loaded with semi-compatible or incompatible inorganic fillers. Such fillers include radiopaque fillers or other general-purpose fillers like silica, clay, graphite, mica, and calcium carbonate. In such an embodiment, the tear strengths and the elongations at yield and break for the material used for the first strip 8 will decrease with the increase of the filler loading.

The base polymeric materials used for the first and second strips 8, 10 can be chemically-compatible. A polymer compatibilizer is introduced to at least one of the polymer materials used for the first and second strips 8, 10 to improve the melt adhesion between the first and second strips 8, 10.

After the tubular body 2 is manufactured, the material used for the first strips 8 can be different from the material used for the second strip 10 with respect to molecular orientation and/or anisotropy in mechanical properties. This will especially be the case with respect to tear strength and elongation at yield and break. Furthermore, the materials used for the first and second strips 8, 10 will be at least partially compatible such that self-adhesion interfacial zones 11 are reliably formable between the strips 8, 10.

The polymer materials used for the strips 8, 10 can be functionally miscible. To be functionally miscible, the two materials used for the strips 8, 10, must have sufficient adhesion to function for the intended use of the instrument, but must have sufficient stress concentrations formed at the interfacial zones 11 between the strips 8, 10 to readily act as a built-in peel groove when the instrument has completed its intended function. In another embodiment, the materials used for the strips 8, 10 are chemically miscible or partially miscible in order to impose the self-adhesion of the strips 8, 10 and create reliable interfacial regions 11 between said strips 8, 10. In one embodiment, the materials used for the strips 8, 10 include melt-processable thermoplastics (e.g., polyethylene, polyvinylidene fluoride, fluorinated ethylene-propylene copolymer, Polyethylene-co-tetrafluoroethylene, plypropylene, polyamide-6, polyamide-6.6, polyamide-11, polyamide-12, polyethylene terephathlate, polybutylenes terephathlate, polycarbonates, polystyrene, etc.) and thermoplastic elastomers ("TPEs") (e.g., polyamide-based TPEs, olefinic TPEs, ionic TPEs, polyester-based TPEs, thermoplastic polyurethanes, etc.).

The polymer material used for the first strip 8 can be a material highly loaded with a radiopaque material. In such an embodiment, the first strip 8 is referred to as the high radiopacity strip(s) 8. In the same embodiment, the material used for the second strip 10 is a polymer material that is not loaded or a material that is lightly loaded with a radiopaque material. In such an embodiment, the second strip 10 is referred to as the low radiopacity strip(s) 10.

As will described in greater detail later in this Detailed Description, the tubular body 2 is inserted into the body of a patient via a surgical site (e.g., entering the chest cavity below the xiphoid process) and directed to a point of treatment (e.g., the pericardial space of a heart). Alternatively, the tubular body 2 is inserted into the body of a patient via a body lumen of a patient (e.g., a blood vessel) and manipulated so it travels along the body lumen to a point of treatment (e.g., a chamber in the heart). A medical device is implanted at the point of treatment via the tubular body 2. To allow the removal of the tubular body 2 without disturbing the implanted medical device (e.g., pacemaker leads), the tubular body 2 is longitudinally split along the interfaces 11 between the strips 8, 10 by simply forcing the sides of the tubular body 2 apart via a fingernail, tool or other implement. The stress concentrations 11 formed at the interfaces 11 between the strips 8, 10 act as a built-in peel groove. The split tubular body 2 is then removed from about the implanted medical device.

Where the tubular body 2 includes a first strip 8 formed from a material that is highly-loaded with a radiopaque material (i.e., the first strip 8 is a high radiopacity strip 8), the travel and positioning of the tubular body 2 within the patient may be monitored via X-ray fluoroscopy.

As will become evident from this Detailed Description, the splittable tubular body 2 in its various embodiments provides the following advantages. First, the tubular body 2 is readily splittable between the two types of strips 8, 10 without the presence of a peeling groove, score or skive. Second, the tubular body 2 is less expensive to manufacture than prior art splittable tubular bodies because a peel groove does not need to be formed on the tubular body 2, and the tubular body 2 can be made in a single simple process, such as co-extrusion, co-injection molding, or co-compression molding.

In embodiments of the tubular body 2 that have first strips 8 made of materials that are highly-loaded with radiopaque materials (i.e., tubular bodies 2 with high radiopacity strips 8), such tubular bodies 2 will also have the following advantages. First, because the tubular body 2 is visible in the human body along its entire length via an X-ray fluoroscope, a physician does not need to estimate the position of the extreme end of the distal tip 4 as is required with prior art tubular bodies that have radiopaque rings implanted in their distal ends. Second, because the tubular body 2 is made from compatible polymers or polymeric compounds without the use of pure metals or metallic compounds, the tubular body 2 has better material compatibility and mechanical integrity than prior art tubular bodies. Third, by having a tubular body 2 with both high radiopacity strips 8 and low radiopacity strips 10, the tubular body is highly flexible, yet highly kink resistant. Other advantageous aspects of the tubular body 2 will become apparent throughout this Detailed Description.

For a better understanding of the first embodiment of the tubular body 2 and its strips 8, 10, reference is now made to FIGS. 2A and 2B. FIG. 2A is a cross-sectional view of the first embodiment of the tubular body 2 taken through section line A-A in FIG. 1. FIG. 2B is a longitudinal cross-sectional view of the first embodiment of the tubular body 2 taken through section line A'-A' in FIG. 2A. As shown in FIGS. 2A and 2B, the first embodiment of the tubular body 2 includes a wall 12 that has an outer circumferential surface 14 and an inner circumferential surface 16. The outer circumferential surface 14 forms the outer surface of the tubular body 2 and the inner circumferential surface 16 defines a lumen 18 through the tubular body 2 that runs the full length of the tubular body 2.

As illustrated in FIG. 2A, each strip 8, 10 forms an integral segment of the wall 12. As shown in FIG. 2A, the tubular body 2, in one embodiment, may have four first strips 8 and four second strips 10 that are formed together (e.g. under a co-extrusion process) to create a wall 12 that is circumferentially continuous and integral along its entire length. In other embodiments, there will be as few as one first strip 8 and one second strip 10. In yet other embodiments, there will be any number of each type of strip 8, 10, including more than four first strips 8 and four second strips 10. Also, in some embodiments, one type of strip 8, 10 will outnumber the other type of strip 8, 10.

In one embodiment with two first strips 8 and two second strips 10, each strip 8, 10 will have a width that comprises approximately 25% of the circumference of the tubular body wall 12. In other embodiments where the strips 8, 10 each account for generally equal percentages of the circumference of the tubular body wall 12, the width of the strips 8, 10, depending on the total number of strips, will range between approximately 2% and approximately 50% of the circumference of the tubular body wall 12.

In one embodiment, one type of strip 8, 10 may constitute a greater percentage of the circumference of the tubular body wall 12. In other words, the first strips 8 may have greater widths than the second strips 10, or vice versa. For example, as illustrated in FIG. 2A, each of the four first strips 8 account for approximately 17% of the circumference of the tubular body wall 12, while each of the second strips 10 each account for approximately 8% of the circumference of the tubular body wall 12. Similarly, in another embodiment with two first strips 8 and two second strips 10, each of the two second strips 10 accounts for approximately 33% of the circumference of the tubular body wall 12, while each of the two first strips 8 accounts for approximately 17% of the circumference of the tubular body wall 12. Again, depending on the number of strips 8, 10, in other embodiments, the width of the strips 8, 10 may range between approximately 2% and approximately 50% of the circumference of the tubular body wall 12. In other embodiments, the width of one or more of the strips 8, 10 will be between approximately 0.1% and approximately 5% to form a micro strip 8, 10.

In one embodiment, one or more of the strips 8, 10 may have a unique percentage of the circumference of the tubular body wall 12. For example, in an embodiment of the tubular body 2 having multiple first strips 8, at least one (if not all) of the first strips 8 has a unique width. Thus, in one embodiment, the widths 8 of the first strips are not all equal. In other embodiments, a similar configuration could exist for at least one (if not all) of the second strips 10 or at least one (if not all) of the strips 8, 10.

In one embodiment, the lumen 18 will have a diameter of between approximately 4 French ("F") and approximately 22 F. In one embodiment, the tubular body 2 will have an outer diameter of between approximately 5 F and approximately 24 F. In one embodiment, the tubular body 2 will have a wall with a thickness of between approximately 0.006" and approximately 0.026".

Figure 4B:
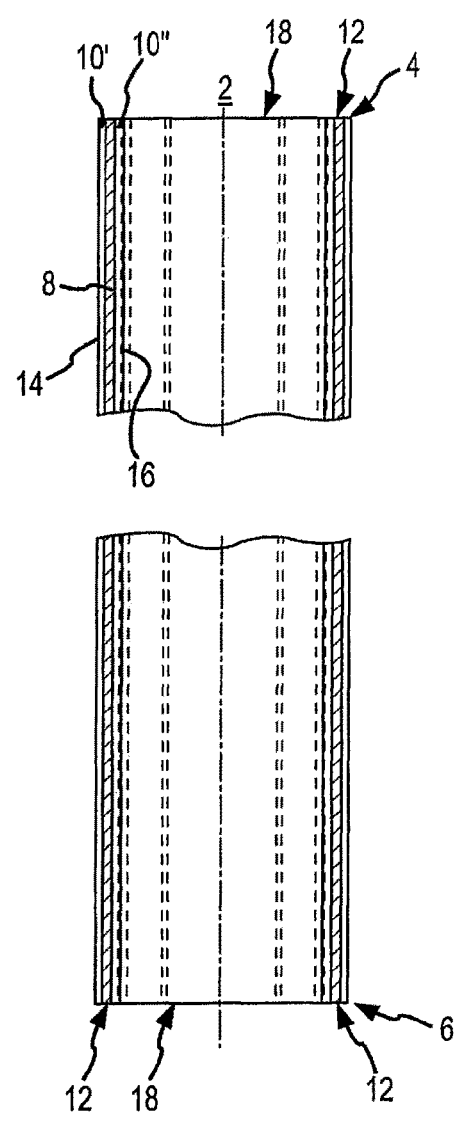
FIG. 4B is a longitudinal cross-sectional view of the second embodiment of the tubular body taken through section line B'-B' in FIG. 4A.

For a discussion of a second embodiment of the invention, reference is now made to FIGS. 3, 4A and 4B. FIG. 3 is a side elevation view of a second embodiment of the radiopaque tubular body 2 having a distal end 4 and a proximal end 6 and being formed of at least two integral longitudinal strips 8, 10. In one embodiment, these strips 8, 10 have different radiopacities. FIG. 4A is a latitudinal cross-sectional view of the second embodiment of the tubular body 2 taken through section line B-B in FIG. 3. FIG. 4B is a longitudinal cross-sectional view of the second embodiment of the tubular body 2 taken through section line B'-B' in FIG. 4A.

As can be understood from FIG. 3 and as is more readily seen in FIGS. 4A and 4B, the second embodiment of the tubular body 2 and its strips 8, are configured similarly to those in the first embodiment of the tubular body 2 as depicted in FIGS. 1, 2A and 2B, except the first strips 8 of the second embodiment are subjacent to layers of second strip material 10', 10" that form the outer and inner circumferential surfaces 14, 16 of the tubular body wall 12. In other words, as illustrated in FIGS. 3, 4A and 4B, the first strips 8 of the second embodiment of the tubular body 2 are sandwiched between an outer layer 10' and an inner layer 10" of second strip material 10.

In other variations of the second embodiment, the first strips 8 of the second embodiment of the tubular body 2 are subjacent to a single layer of second strip material 10. For example, in a first variation of the second embodiment of the tubular body 2, as depicted in FIGS. 4C and 4D, which are, respectively, a latitudinal cross-sectional view of the tubular body 2 taken through section line B-B in FIG. 3 and a longitudinal cross-sectional view of the tubular body 2 taken through section line B"-B" in FIG. 4C, the first strips 8 are subjacent to a single layer of second strip material 10, which is an outer layer 10'. Thus, as depicted in FIGS. 4C and 4D, the second strip outer layer 10' forms the outer circumferential surfaces 14 of the tubular body wall 12 and the first strips 8 form segments of the inner circumferential surface 16 of the tubular body wall 12.

Similarly, in a second variation of the second embodiment of the tubular body 2, as depicted in FIGS. 4E and 4F, which are, respectively, a latitudinal cross-sectional view of the tubular body 2 taken through section line B-B in FIG. 3 and a longitudinal cross-sectional view of the tubular body 2 taken through section line B'''-B''' in FIG. 4E, the first strips 8 are subjacent to a single layer of second strip material 10, which is an inner layer 10". Thus, as depicted in FIGS. 4E and 4F, the second strip inner layer 10" forms the inner circumferential surfaces 16 of the tubular body wall 12 and the first strips 8 form segments of the outer circumferential surface 14 of the tubular body wall 12.

Figure 6A:
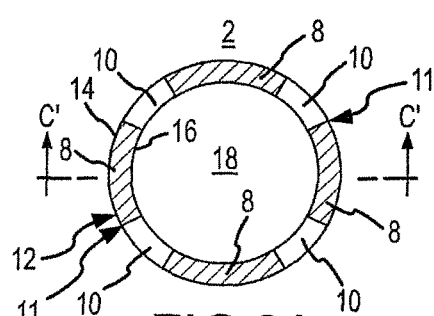
FIG. 6A is a latitudinal cross-sectional view of the third embodiment of the tubular body taken through section line C-C in FIG. 5.
Figure 5:
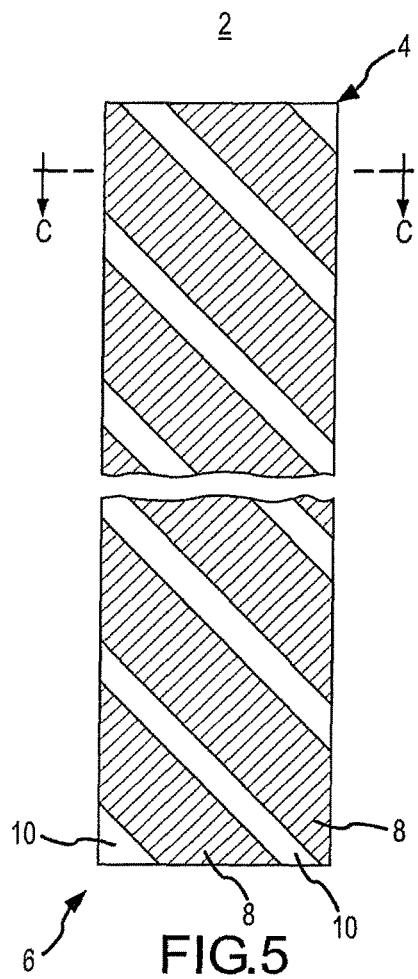
FIG. 5 is a side elevation view of the present invention according to a third embodiment, including a splittable tubular body for a catheter or sheath, wherein the tubular body includes a distal end and a proximal end and is formed of at least two integral longitudinal helical strips of different material.

For a discussion of a third embodiment of the invention, reference is now made to FIGS. 5, 6A and 6B. FIG. 5 is a side elevation view of a third embodiment of the tubular body 2 having a distal end 4 and a proximal end 6 and being formed of at least two integral longitudinal helical strips 8, 10. These strips 8, 10 can have different radiopacities. FIG. 6A is a latitudinal cross-sectional view of the third embodiment of the tubular body 2 taken through section line C-C in FIG. 5. FIG. 6B is a longitudinal cross-sectional view of the third embodiment of the tubular body 2 taken through section line C'-C' in FIG. 6A.

As shown in FIGS. 5, 6A and 6B, in the third embodiment of the tubular body 2, its strips 8, 10 are configured similarly to those in the first embodiment of the tubular body 2 as depicted in FIGS. 1, 2A and 2B, except the strips 8, 10 of the second embodiment extend spirally or helically along the length of the third embodiment of the tubular body 2.

Figure 8A:
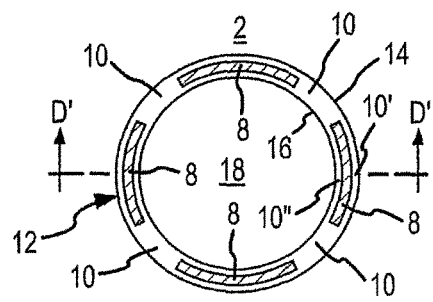
FIG. 8A is a cross-sectional view of the fourth embodiment of the tubular body taken through section line D-D in FIG. 7.
Figure 7:
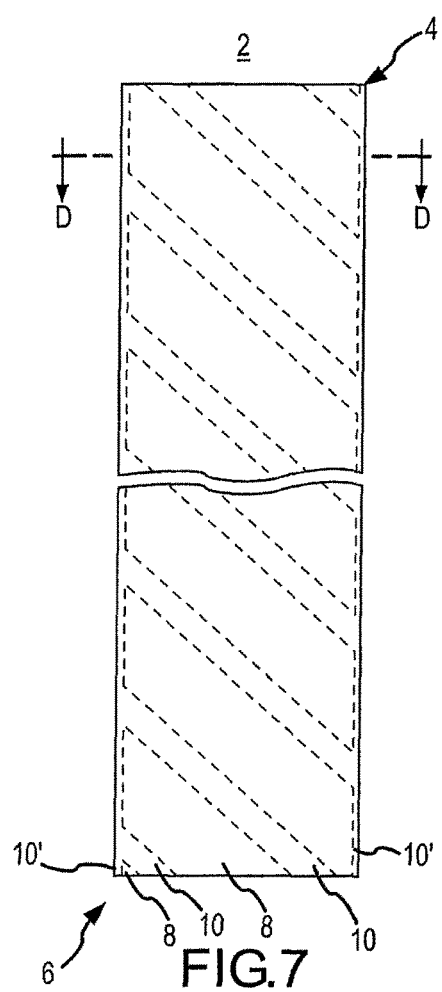
FIG. 7 is a side elevation view of the present invention according to a fourth embodiment, including a splittable tubular body for a catheter or sheath, wherein the tubular body includes a distal end and a proximal end and is formed of at least two integral longitudinal helical strips of different material.

For a discussion of a fourth embodiment of the invention, reference is now made to FIGS. 7, 8A and 8B. FIG. 7 is a side elevation view of a fourth embodiment of the tubular body 2 having a distal end 4 and a proximal end 6 and being formed of at least two integral longitudinal helical strips 8, 10. These strips 8, 10 can have different radiopacities. FIG. 8 is a latitudinal cross-sectional view of the fourth embodiment of the tubular body 2 taken through section line D-D in FIG. 7. FIG. 8B is a longitudinal cross-sectional view of the fourth embodiment of the tubular body 2 taken through section line D'-D' in FIG. 8A.

As can be understood from FIG. 7 and as is more readily seen in FIGS. 8A and 8B, the fourth embodiment of the tubular body 2 and its helical strips 8, 10 are configured similarly to those in the third embodiment of the tubular body 2 as depicted in FIGS. 5, 6A and 6B, except the helical first strips 8 of the fourth embodiment are subjacent to layers of second strip material 10', 10" that form the outer and inner circumferential surfaces of the tubular body wall 12. In other words, as illustrated in FIGS. 7, 8A and 8B, the helical first strips 8 of the fourth embodiment of the tubular body 2 are sandwiched between an outer layer 10' and inner layer 10" of second strip material 10.

In other variations of the fourth embodiment, the first strips 8 of the fourth embodiment of the tubular body 2 are subjacent to a single layer of second strip material 10. For example, in a first variation of the fourth embodiment of the tubular body 2, as depicted in FIGS. 8C and 8D, which are, respectively, a latitudinal cross-sectional view of the tubular body 2 taken through section line D-D in FIG. 7 and a longitudinal cross-sectional view of the tubular body 2 taken through section line D"-D" in FIG. 8C, the first strips 8 are subjacent to a single layer of second strip material 10, which is an inner layer 10". Thus, as depicted in FIGS. 8C and 8D, the second strip inner layer 10" forms the inner circumferential surface 16 of the tubular body wall 12 and the first strips 8 form segments of the outer circumferential surface 14 of the tubular body wall 12.

Similarly, in a second variation of the fourth embodiment of the tubular body 2, as depicted in FIGS. 8E and 8F, which are, respectively, a latitudinal cross-sectional view of the tubular body 2 taken through section line D-D in FIG. 7 and a longitudinal cross-sectional view of the tubular body 2 taken through section line D'"-D'" in FIG. 8E, the first strips 8 are subjacent to a single layer of second strip material 10, which is an outer layer 10'. Thus, as depicted in FIGS. 8E and 8F, the second strip outer layer 10' forms the outer circumferential surface 14 of the tubular body wall 12 and the first strips 8 form segments of the inner circumferential surface 16 of the tubular body wall 12.

The first strips 8 and the second strips 10 can be formed from two compatible polymers or polymeric compounds into an integral tubular body 2 via co-extrusion, co-injection molding, or co-compression molding processes. Candidate polymeric materials include thermoplastic and thermosetting polymer systems.

The first strips 8 may be formed of material that is heavily filled with a biocompatible filler of heavy metal or a biocompatible metallic compound that gives rise to high radiopacity under X-ray radiation. The functional width and wall thickness (i.e., percentage of the circumference of the tubular body wall 12) necessary for visibility via X-ray fluoroscopy will vary depending on the degree of radiopacity for a first strip 8 (i.e., high radiopacity strip 8). For example, where a first strip 8 has a high degree of radiopacity (due to the radiopaque nature of the filler of metal or metallic compound impregnated in the polymer and/or due to the percentage of the metal or metallic compound in the polymer), narrower and thinner first strips 8 will suffice. On the other hand, where a first strip 8 has a lower degree of radiopacity, wider and thicker first strips 8 will be required to achieve the necessary visibility via X-ray fluoroscopy.

The first strips 8 (i.e., high radiopacity strips 8), if they are made from elastomeric polymer materials loaded with radiopaque fillers, provide kink resistance for the tubular body 2 in addition to providing the ability to be visualized within a patient's body via X-ray fluoroscopy. In a preferred embodiment, the first strips 8 will be a tungsten-impregnated thermoplastic elastomer, including thermoplastic polyurethane, polyether block amide, and etc. The amount of tungsten used will depend on the degree of radiopacity required and the thermoplastic elastomer. For example, when the strips are formed of PEBAX, the first strip can be loaded with 60-5% by weight tungsten, and preferably 80-85% by weight tungsten.

The second strips 10 (i.e., low radiopacity strips 10) are either not loaded with radiopaque fillers or are lightly loaded. Thus, the second strips 10 have a low radiopacity under X-ray radiation and provide mechanical strength and durability for the tubular body 2.

For melt processing purposes, the selection of the pairs of polymers used for the strips 8, 10 is primarily based on the level of chemical compatibility, balance of mechanical properties, and melt processability between the pairs of polymers. Different grades of polymers having the same constituent chemical species (e.g., various thermoplastic elastomers, including polyether block amides, polyurethanes, olefinics, styrenics, polyesters, polyethers, and etc.) may be used for the pairs. Pairs of thermoplastics and thermoplastic elastomers can also be used (e.g., polyamides with polyether block amides, polyesters with polyether-co-esters). Other polymer pairs are possible with use of polymer compatibilization technologies.

For radiopaque tubular bodies 2, one base polymer from a polymer pair must be filled with heavy metals or metallic compounds using blending and compounding technologies via either melt or solvent processes. The heavy metals and compounds shall be biocompatible (e.g., barium, tungsten, tantalum, platinum, gold, bismuth, zirconium, niobium, titanium, bismuth oxychloride, barium sulfate, bismuth trioxide, iodine, iodide, etc. and their compounds). In one embodiment, the biocompatible radiopaque filler will contain at least one element with an atomic number of from about 22 to about 83.

Filler of a heavy metal or a metallic compound may not be compatible with a selected base polymer, and may cause a drastic decrease in mechanical properties in the heavily loaded polymer compound. To increase the loading level of radiopaque filler and to improve the compatibility of the filler with the base polymer, a compatibilizer or coupling agent can be used for the polymer compound.

As previously noted, the tubular bodies 2 are peelable (i.e., splittable) at one or more border(s) (i.e., interface(s)) between the two types of strips 8, 10. To longitudinally split the tubular body 2, opposite sides of the interior circumferential surface 16 are simply forced apart via a fingernail, tool or other implement. The change in material at the borders between the strips 8, 10 creates a stress concentration point that acts as a built in peel groove along which the tubular body 2 splits when peeled. Thus, no integral peeling groove is needed. However, in some embodiments, as indicated in FIG. 9, an integral peel groove, skive or score 20 is provided to supplement the peelability of the tubular body 2. This can be readily implemented in the embodiments illustrated in FIGS. 1-4. Ideally, this peel groove, skive or score 20 is aligned longitudinally with a boarder between a pair of strips 8, 10. However, the peel groove, skive or score 20 can be located in one of the strips 8, 10 as indicated in FIG. 9. A tubular body 2 can have one or more peel grooves, skives or scores. The peel groove, score or skive 20 can be located in the inner and/or outer circumferential surface of the tubular body 2.

Many of the aforementioned embodiments employ at least one strip 8, formed of a material loaded with a radiopaque material. However, the strips 8, 10 can be formed of polymers that are not loaded with a radiopaque or other materials. For example, the first strips 8 can be formed from a polymer that is dissimilar from the polymer forming the second strips 10. The dissimilarity between the two polymers forming the two strips 8, 10 results in a stress concentration along the interfacial boundary between the two strips 8, 10. The stress concentration serves as a split/peel feature in the tubular body 2 for splitting/peeling the body 2.

The polymers of the strips 8, 10 can be the same polymer, but dissimilar because they have dissimilar molecular orientations. The polymers of the strips 8, 10 can be the same polymer, but dissimilar because they have different toughness, hardness, rigidity, and/or etc. For example, the first or splitting strip 8 can be formed of PEBAX having a durometer value of approximately 70 D, and the second or non-splitting strip 10 is formed of PEBAX having a durometer value of approximately 30-40 D.

Figure 10:
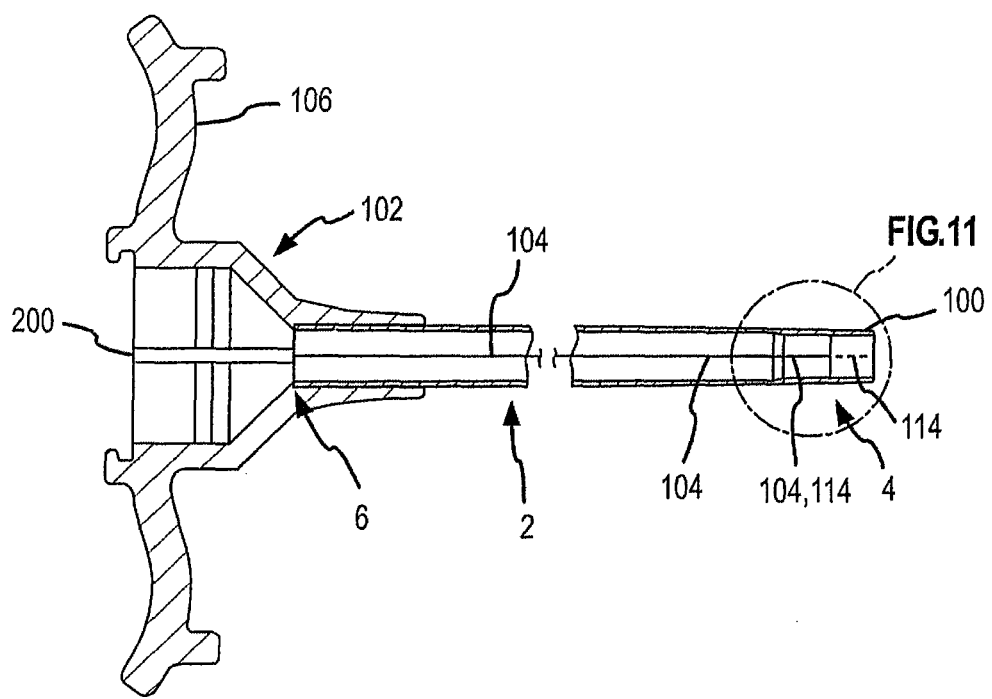
FIG. 10 is a longitudinal section elevation of the tubular body with an atraumatic tip.
Figure 11:
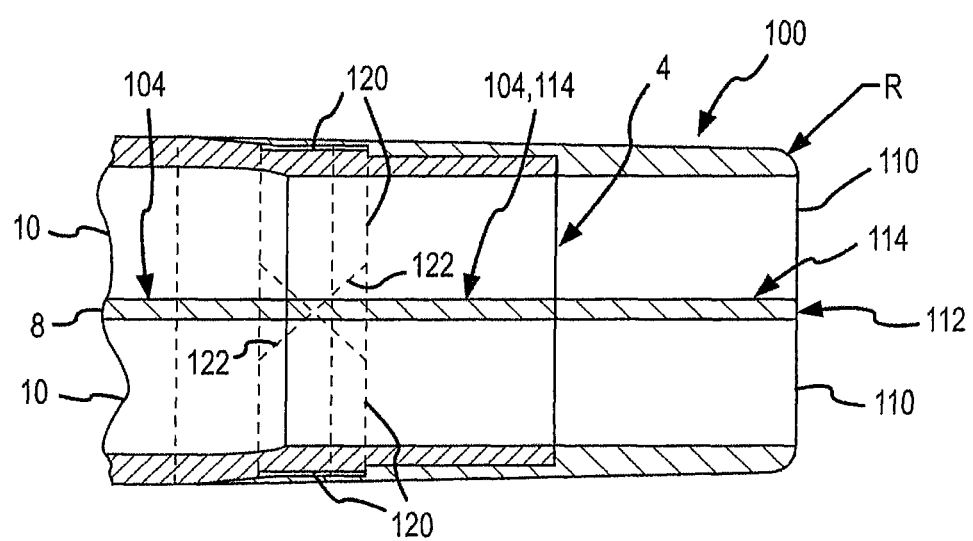
FIG. 11 is an enlarged, cross-sectional view of the portion of FIG. 10 shown in dashed lines on that figure.

For a discussion of an embodiment of the tubular body 2 that includes a splittable soft atraumatic tip 100, reference is now made to FIGS. 10 and 11. FIG. 10 is a longitudinal section elevation of the tubular body 2 with a soft atraumatic tip 100. FIG. 11 is an enlarged section elevation of the soft atraumatic tip 100 coupled to the distal end 4 of the tubular body 2 depicted in FIG. 10.

As shown in FIG. 10, the tubular body 2 can include an interlock 102 coupled to the proximal end 6 and a soft atraumatic tip 100 coupled to the distal end 4. The tubular body 2 includes one or more longitudinally extending peel/split mechanisms 104 for facilitating the peeling/splitting apart of the tubular body 2 to allow the removal of the tubular body from about an implanted medical device (e.g., pacemaker leads) without disturbing the implanted device.

The tubular body 2 can have a durometer value of approximately 70 D. The soft atraumatic tip 100 will have a durometer value of approximately 20-40 D.

The interlock 102 has a splittable housing. In one embodiment, the interlock 102 includes wings 106 for applying splitting forces to the interlock 102 and causing splitting/peeling of the interlock 102, the tubular body 2 and the tip 100. The interlock 102 includes a longitudinally extending splitting mechanism 200 forming a longitudinally extending stress concentration that facilitates the splitting of the housing of the interlock 102. In one embodiment, the splitting mechanism 200 is a score, skive or groove 200. In one embodiment, the splitting mechanism 200 is a strip 200 of a polymer material that is different from the polymer material forming the rest of the interlock 102. The material forming the strip 200 is different from the material forming the rest of the interlock in a manner similar to those discussed in this Detailed Description with respect to the tubular body 2 and the tip 100. The dissimilarity between the polymer of the strip 200 and the polymer of the rest of the interlock 102 results in a stress concentration extending along the interfacial zone between the two materials. Like the tubular body 2 and the tip 100, the stress concentration facilitates the splitting of the interlock 200.

The strip 200 can be formed from a material that is softer than the material used for the rest of the interlock 102. The strip 200 can be formed from a material that is harder than the material used for the rest of the interlock 102. The strip 200 and the rest of the interlock 102 can be formed via polymer molding processes known in the art. The housing of the interlock 102 can be formed from polymers such as High Durometer PEBAX, High Density HDPE, etc. and the split strip in the housing is formed from polymers such as Low Durometer PEBAX, Low Density HDPE, etc. While FIG. 10 depicts a splittable interlock 102, other medical devices (e.g., valves, junctions, fittings, etc.) coupled to a splittable tubular body 2 can be made splittable by being provided with a splitting mechanism 200 as discussed above.

Each peel/split mechanism 104 of the tubular body 2 can be an interfacial zone (i.e., boundary) 11 between two longitudinally extending strips of different material 8, 10 that form a stress concentration 11, as previously provided in detail in this Detailed Description (see FIGS. 1 and 2A). Each peel/split mechanism 104 can be a longitudinally extending line scored/skived into the wall 12 of the tubular body 2. The scored/skived line 104 can be formed in the interior circumferential surface 16 of the wall 12 (e.g., see the peel groove 20 in FIG. 9). The scored/skived line 104 can be formed in the exterior circumferential surface 14 of the wall 12. In one embodiment, the scored/skived line 104 is formed in both the exterior and interior circumferential surfaces 14, 16 of the wall 12.

As shown in FIG. 11, the splittable soft atraumatic tip 100 can be formed from a first soft material 110. The first material 100 can be loaded with a radiopaque filler to enhance the visibility of the tip 100 during fluoroscopy. The tip 100 is bonded (e.g., reflowed) to the distal end 4 of the tubular body 2.

In order to allow the tip 100 to readily split/peel along with the body 2 to allow the tubular body 2 to be removed from about an implanted medical device (e.g., pacemaker leads), one or more peel/split mechanisms 114 can longitudinally extend along the tip 100. The split/peel mechanisms 114 are scored/skived lines 114 longitudinally extending along the interior circumferential surface of the tip 100. The longitudinally extending scored/skived lines 114 can be in the exterior circumferential surface of the tip 100. The longitudinally extending scored/skived lines 114 can be in both the exterior and interior circumferential surfaces of the tip 100.

In order to allow the tip 100 to readily split/peel along with the body 2, the split/peel mechanisms 114 can be longitudinally extending interfaces 114 (i.e., boundaries) between longitudinally extending strips of first and second soft polymeric materials 110, 112. Specifically, in one embodiment, the second soft polymeric material 112 is co-extruded, co-injection molded, or co-compression molded with the first soft polymeric material 110 in a manner similar to the process previously described in this Detailed Description with respect to the tubular body 2. Split/peel mechanisms 114 are formed by the interfaces 114 between the first and second soft polymeric materials 110, 112. Stress concentrations 114, which facilitate the splitting/peeling of tip 100, result along the interfaces 114.

In order to facilitate the splitting/peeling of the tip 100, the first and second polymeric materials 110, 112 will differ from each other in one of the ways previously described in this Detailed Description with respect to the tubular body 2. For example, the second polymeric material 112 can be a version of the first polymeric material 110 that is heavily loaded with a radiopaque material. The first polymeric material 110 is PEBAX can have a durometer value of 20-40 D, and the second polymeric material 112 is the same type of PEBAX, except it is loaded with 75-80 percent tungsten.

Each of the strips 110, 112 can account for generally equal percentages of the circumference of the wall of the tip 100. In one such embodiment, the width of the strips 110, 112 will depend on the total number of strips and will range between approximately 2% and approximately 50% of the circumference of the wall of the tip 100.

One type of strip 110, 112 can constitute a greater percentage of the circumference of the wall of the tip 100. In other words, the second strips 112 may have greater widths than the first strips 110, or vice versa. The width of the strips 110, 112 may range between approximately 2% and approximately 50% of the circumference of the wall of the tip 100. In other embodiments, the width of one or more of the strips 110, 112 will be between approximately 0.1% and approximately 5% to form a micro strip 110, 112.

Figure 13:
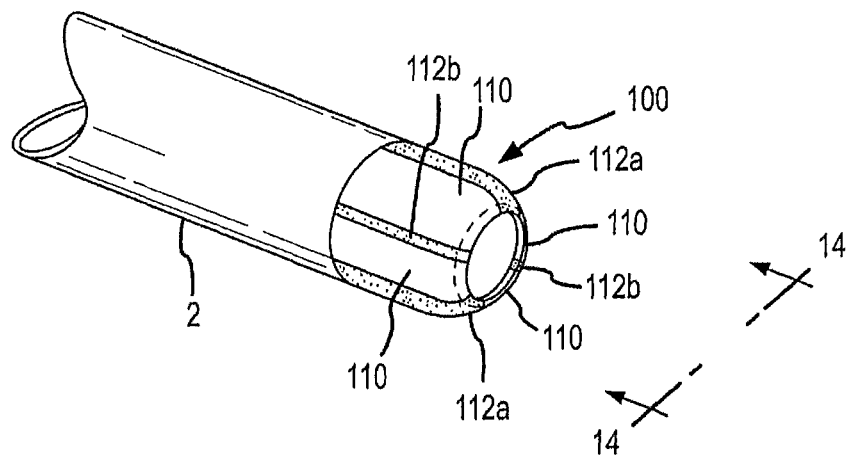
FIG. 13 is an isometric view of an atraumatic tip including a pair of wide high-radiopacity strips and a pair of narrow high-radiopacity strips.
Figure 14:
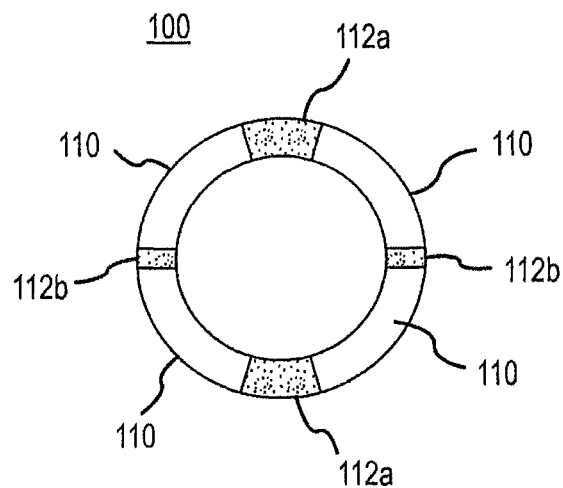
FIG. 14 is a distal end view of the atraumatic tip depicted in FIG. 13.

As depicted in FIGS. 13 and 14, which are, respectively, isometric and distal end views of an atraumatic tip 100, the atraumatic tip 100 can include a pair of wide high-radiopacity strips 112a and a pair of narrow high-radiopacity strips 112b. The wide high-radiopacity strips 112a run longitudinally along the tip 100 and are located 180 degrees from each other about the outer circumference of the tip 100. The narrow high-radiopacity strips 112a run longitudinally along the tip 100 and are located 180 degrees from each other about the outer circumference of the tip 100.

The tip 100 is provided on a tubular body 2 of a catheter or sheath wherein the body 2 is pre-curved in two planes that are perpendicular to each other. The tip 100 is mounted on the distal end of the body 2 such that the pair of wide high-radiopacity strips 112a are coplanar with a plane in which a first curve of the body 2 exists, and the pair of narrow high-radiopacity strips 112a are coplanar with a plane in which a second curve of the body 2 exists. A physician can view the strips 112a, 112b via fluoroscopy and, as a result, understand the orientation of the pre-curved portions of the tubular body 2 within the patient. Thus, the strips 112a, 112b facilitate the physician's proper torquing and displacement of the tubular body 2 within the patient to achieve optimal placement of the distal end of the tubular body 2.

While FIGS. 13 and 14 depict a tip 100 with two pairs of high-radiopacity strips 112a, 112b that are oriented parallel to each other, in other embodiments the tip will have fewer or more pairs of strips 112 and/or the strips will have non-parallel orientations relative to each other. For example, the pre-curved tubular body 2 can have a single curve plane, and the tip 100 has a single pair of high radiopacity strips 112 that corresponds to the single curve plane of the tubular body 2. The pre-curved tubular body 2 can have three or more curve planes, and the tip 100 has three or more pairs of high radiopacity strips 112, each pair of strips 112 corresponding to a respective curve plane of the tubular body 2. The pre-curved tubular body 2 can have curves that exist in planes that are not parallel to each other, and the tip 100 has an equivalent number of pairs of strips 112 that have the same angular relationship to each other as the corresponding angular relationship between the corresponding curve planes.

As can be understood from FIGS. 9-12, each peel/split mechanism 114 can be a score/skive line used in combination with an interface/boundary between two strips of different material. In other words, each interface/boundary will be supplemented with a score/skive line extending along the length of the interface/boundary. The score/skive line will be located at some other location on one or more of any one of the strips 110, 112. There can be one or more score/skive lines. The score/skive lines can be located in the inner and/or outer circumferential surfaces of the tip 100.

As illustrated in FIG. 10, the split/peel mechanisms 114 of the tip 100 are aligned with the corresponding split/peel mechanisms 104 of the body 2. Thus, when the wings 106 of the interlock 102 are forced apart to cause the interlock 102 and body 2 to split/peel along the split/peel mechanisms 104 of the body 2, the split resulting in the wall 12 of the body 2 propagates along the split/peel mechanisms 114 of the tip 100 from the split/peel mechanisms 104 of the body 2.

To enhance the visibility of the tip 100 during fluoroscopy, a greater number of strips of high-radiopacity material 112 can be provided. For example, in one embodiment, the soft tip 100 includes one, two, three, four or more longitudinally extending strips of high-radiopacity material 112. To further increase the visibility of the tip 100 during fluoroscopy, the strips of high-radiopacity material 112 can be made relatively wide with respect to the strips of first material 110.

To enhance the visibility of the tip 100 as compared to the visibility of the body 2 during fluoroscopy, the number of radiopaque strips 112 for the tip 100 can exceed the number of radiopaque strips 8 for the body 2. For example, in one embodiment, the tip 100 has four radiopaque strips 112 and the body 2 has two radiopaque strips 8. Two of the tip's radiopaque strips 112 can be longitudinally aligned with the body's two radiopaque strips 8. Thus, the aligned strips 8, 112 can be used as peeling mechanisms for peeling the body and tip apart. The tip's other two (i.e., non-aligned) radiopaque strips 112 simply increase the radiopacity of the tip 100 and do not facilitate peeling of the tip 100.

To facilitate the ease of manufacturing a splittable tubular body 2 having a splittable tip 100, the tip 100 can be provided with many peeling mechanisms (e.g., split/peel strips 114). As a result, the tip 100 can be placed on the distal end of the tubular body 2 without having to worry about aligning the peeling mechanisms of the tip 100 with the peeling mechanisms of the tubular body 2. This is because the large number of peeling mechanisms on the tip 100 assures sufficient alignment between at least one of the tip peeling mechanisms and a peeling mechanism of the tubular body 2, thereby allowing the splitting of the tubular body 2 to propagate through the tip 100.

A tip 100 can have many peeling mechanisms, the tip 100 will have approximately four to approximately twelve split/peel strips 114 having widths of approximately 0.003 inches to approximately 0.025 inches. In one embodiment, the tip 100 will have approximately eight split/peel strips 114 having widths of approximately 0.02 inches.

As depicted in FIG. 11, in one embodiment, to enhance the visibility of the tip 100 during fluoroscopy, a marker band 120 formed from a highly radiopaque material (e.g. platinum) is imbedded between the tubular body 2 and the tip 100. As disclosed in U.S. patent application Ser. Nos. 11/052,617 (filed Feb. 4, 2005) and 10/609,206 (filed Jun. 26, 2003), both of which are incorporated by reference into this Detailed Description in their entireties, the marker band 120 is notched with one or more single or double V-notches 122 to facilitate splitting of the tubular body 2, tip 100 and band 120. Each V-notch 122 is aligned with a split/peel mechanism 114 of the tip 100. In other embodiments, the notch 122 has other shapes or configurations that facilitate the splitting of the marker band 120 (e.g., arcuate shape, skives, slots, penetrations, etc.) In other embodiments the marker band 120 does not have a notch 122, but is simply thin enough to fail where the tip 100 splits/peels when the tubular body 2 is being split/peeled.

The tip 100 can have a wall thickness that is generally equal to that of the tubular body 2. In other embodiments, the tip 100 has a wall thickness that is greater or less than the wall thickness of the tubular body 2.

Figure 12:
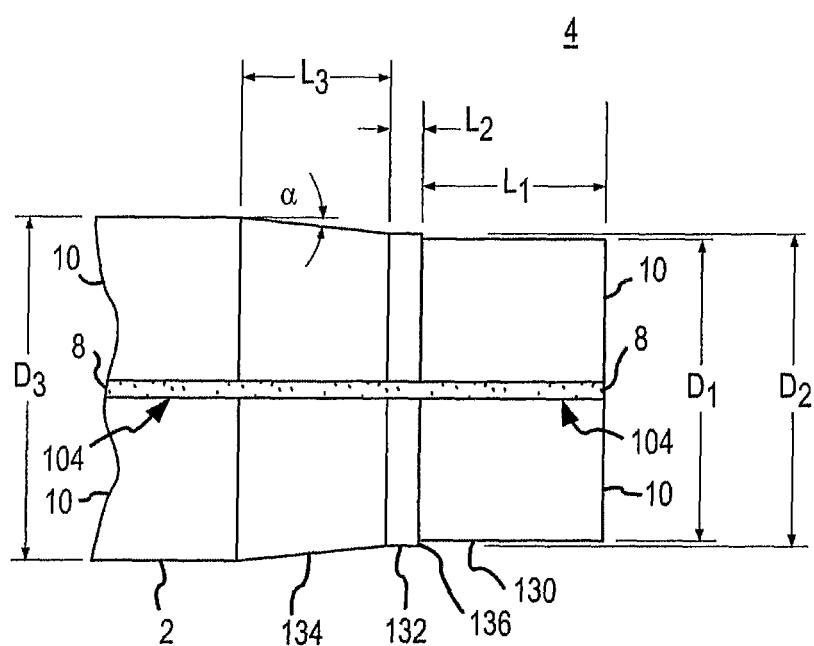
FIG. 12 is an enlarged, side elevation view of the distal end of the tubular body prior to the attachment of the tip.

Reference is now made to FIG. 12 for a discussion of a method of manufacturing a splittable/peelable tubular body 2 having a soft atraumatic splittable/peelable tip 100, as depicted in FIGS. 10 and 11. FIG. 12 is an enlarged side elevation view of the distal end 4 of the tubular body 2.

As can be understood from FIG. 12, a tubular body 2 having one or more split/peel mechanisms 104 is placed over a mandrel. The split/peel mechanisms 104 can be peel grooves or score/skive lines 114 longitudinally extending along the length of the tubular body 2 as previously discussed in this Detailed Description. The split/peel mechanisms 104 can be interfaces/boundaries 104 formed between longitudinally extending strips of co-extruded, co-injection molded, or co-compression molded first and second materials 8, 10 (see FIGS. 1-9) as previously discussed in this Detailed Description.

The distal end 4 of the tubular body 2 can be profile ground to appear as depicted in FIG. 12. Specifically, in one embodiment, the distal end 4 has a distal most section 130, an intermediate section 132, and a tapered section 134. In one embodiment, the distal most section 130 has a diameter $D_1$ of approximately 0.120 inches and a length $L_1$ of approximately 0.070 inches. A step 136 transitions from the distal most section 130 to the intermediate section 132, which has a diameter $D_2$ of approximately 0.125 inches and a length $L_2$ of approximately 0.013 inches. Over a length $L_3$ of approximately 0.057 inches, the tapered section 134 transitions from the intermediate section 132 to the non-ground diameter $D_3$ of the tubular body 2, which is approximately 0.135 inches. The surface of the tapered section 134 extends at an angle σ that is approximately 5 degrees from being parallel to the surface of the non-ground diameter $D_3$ of the tubular body 2. The preceding values are exemplary. In other embodiments, the preceding diameters, lengths and angles will vary without departing from the scope of the invention.

The marker band 120 can be placed about the intermediate section 132 and a portion of the tapered portion 134 such that the most distal edge of the marker band 120 coincides with the edge of the step 136, as indicated in FIG. 11. Each V-notch 122 of the marker band 120 is aligned with the split/peel mechanism 104 of the tubular body 2.

A soft atraumatic splittable/peelable tip 100 is placed over the profile ground portion of the distal end 4 of the tubular body 2. The tip 100 can be PEBAX with a durometer value of approximately 20-40 D. This will be considerably softer than the durometer value of the tubular body 2, which will be approximately 70 D in one embodiment.

The tip 100 can be oriented upon the distal end 4 of the tubular body 2 such that the split/peel mechanisms 114 of the tip 100 are aligned to correspond with the split/peel mechanisms 104 of the tubular body 2. The split/peel mechanisms 114 of the tip 100 can be interface/boundaries 114 between co-extruded, co-injection molded, or co-compression molded strips of first and second polymeric materials 110, 112 that extend longitudinally along the tip 100.

The soft tip 100 is bonded to the ground portion of the distal end 4 of the tubular body 2. The bonding can be performed via thermal means. For example, the tip 100 and tubular body 2 are supported on a mandrel and a short section of PTFE heat shrink tube is placed over the distal end 2 and the tip 100. This arrangement is then placed in a reflow-tipping machine to bond the tip 100 to the distal end 4. In other embodiments, chemical, sonic, RF or other means are utilized to bond the tip 100 to the distal end 4. Where a marker band 120 is present, the band 120 will be sandwiched between the tip 100 and the tubular body 2 as shown in FIG. 11.

The split/peel mechanisms 114 of the tip 100 can be peel grooves or score/skive lines 114 longitudinally extending along the tip 100. In such embodiments, the peel grooves or score/skive lines 114 will be formed during the bonding process via molding grooves in the mandrel. The peel grooves or score/skive lines 114 can be cut into the tip 100 after the tip 100 has been bonded to the distal end 4. The score/skive line depth and angle will vary depending upon the peel/split force desired for the tubular body 2.

The tubular body 2 with its attached tip 100 is removed from the mandrel and trimmed to the correct length. A radius R of approximately 0.010 inches is then ground or thermally formed in a radius die at the distal end of the tip 100 (see FIG. 11).

Many of the aforementioned embodiments of the tip 100 employ at least one strip 110, 112 that is formed of a material loaded with a radiopaque material. However, the strips 110, 112 can be formed of polymers that are not loaded with radiopaque or other materials. For example, the first strips 112 can be formed from a polymer that is dissimilar from the polymer forming the second strips 110. The dissimilarity between the two polymers forming the two strips 110, 112 results in a stress concentration along the interfacial boundary between the two strips 110, 112. The stress concentration serves as a split/peel feature in the tubular body 2 for splitting/peeling the body 2.

The polymers of the strips 110, 112 can be the same polymer, but dissimilar because they have dissimilar molecular orientations. The polymers of the strips 110, 112 can be the same polymer, but dissimilar because they have different toughness, hardness, rigidity, and/or etc. For example, the first or splitting strip 112 is formed of PEBAX having a durometer value of approximately 70 D, and the second or non-splitting strip 110 is formed of PEBAX having a durometer value of approximately 20-40 D. The polymers of the strips 110, 112 are dissimilar because they are different polymers.

A catheter or sheath employing a splittable/peelable tubular body 2 with the described splittable/peelable soft atraumatic tip 100 is advantageous over the prior art for several reasons. First, the tip 100 can be visible via fluoroscopy. Second, the tubular body 2 is peelable/splittable over its entire length, including its tip 100. As a result, the tubular body 2 may be removed from about an implanted medical device (e.g., pacemaker leads) without disturbing the medical device. Third, the soft atraumatic tip 100 reduces the potential for tissue dissection, which can sometimes occur with stiffer, less atraumatic tipped tubular bodies.

In use, a puncture is made with a thin walled needle through the skin and into a blood vessel. A guidewire is then placed through the needle into the blood vessel and the needle is withdrawn. An intravascular introducer is advanced over the guidewire into the lumen of the blood vessel. The tubular body 2 is inserted into the introducer and manipulated so it travels along the blood vessel to the point of treatment (e.g., a chamber in the heart). The travel and positioning of the tubular body 2 within the patient is monitored via X-ray fluoroscopy.

In use, the tubular body 2 is inserted into the body of a patient via a surgical site (e.g., entering the chest cavity below the xiphoid process). A guidewire is used to direct the tubular body 2 to a point of treatment (e.g., the pericardial space of a heart). The travel and positioning of the tubular body 2 within the patient is monitored via X-ray fluoroscopy.

Although the present invention has been described with reference to preferred embodiments, persons skilled in the art will recognize that changes may be made in form and detail without departing from the spirit and scope of the invention.

We claim:

1. A method of attaching a peelable atraumatic tip to a distal end of a peelable tubular body of a catheter or sheath, the method comprising:
    placing the tubular body on a mandrel, the body including a first peel mechanism longitudinally extending along the body, wherein the first peel mechanism is formed by a longitudinally extending region of interfacial bonding between first and second longitudinally extending strips of respective first and second polymeric material;
    placing the tip onto the distal end of the body, the tip including a second peel mechanism longitudinally extending along the tip;
    aligning the second peel mechanism to longitudinally coincide with the first peel mechanism; and
    joining the tip to the distal end.

2. The method of claim 1, wherein the tip is generally softer than the tubular body.

3. The method of claim 2, wherein the second peel mechanism is formed by a longitudinally extending region of interfacial bonding between third and fourth longitudinally extending strips of polymeric material.

4. The method of claim 3, wherein the interfacial bonding between the third and fourth strips results in a region of stress concentration extending along the region of interfacial bonding between the third and fourth strips.

5. The method of claim 1, wherein the polymeric material of the first strip comprises a first amount of a first radiopaque filler, wherein the polymeric material of the second strip comprises a second amount of a second radiopaque filler, and wherein the first amount is greater than the second amount.

6. The method of claim 1, wherein the tip has a circular cross section, with a circumference, and the first strip has a width of between 0.1% and 5% of the circumference of the tip.

7. The method of claim 1, further comprising third and fourth longitudinally extending strip of polymeric material, wherein the polymeric material of the third strip comprises a third amount of radiopaque filler, wherein the polymeric material of the second strip comprises a second amount of a second radiopaque filler, and wherein the third amount is greater than the fourth amount, and the third strip is wider than the first strip.

8. The method of claim 1, wherein each strip forms at least a portion of an outer surface of the tubular body.

9. The method of claim 1, wherein a region of stress concentration extends along the region of interfacial bonding.

10. The method of claim 9, wherein the region of stress concentration facilitates the splitting of the tip along the first peel mechanism.

11. The method of claim 1, wherein the first polymeric material is dissimilar from, but chemically compatible with, the second polymeric material.

12. The method of claim 1, wherein the first strip is formed of a polyether block amide having a durometer value of approximately 70 D and the second strip is formed of a polyether block amide having a durometer value of 20-40 D.

13. The method of claim 1, wherein the first polymeric material has a molecular orientation that is different from a molecular orientation of the second polymeric materiel.

14. The method of claim 1, wherein the first polymeric material is loaded with a greater amount of inorganic filler that the second polymeric material.

15. The method of claim 1, wherein the first polymeric material is chemically incompatible with the second polymeric material, and a polymer compatibilizer is introduced into at least one of the polymeric materials to improve melt adhesion between the first and second strips of polymeric material.

16. The method of claim 1, further comprising imbedding a circular radiopaque band below an outer surface of the tip and including a notch aligned with the second peel mechanism.

17. The method of claim 1, wherein the second peel mechanism is formed by a peel groove.

18. The method of claim 1, wherein the second peel mechanism is formed by a score/skive line.

\* \* \* \* \*